(12) United States Patent
Keller et al.

(10) Patent No.: US 9,511,143 B2
(45) Date of Patent: Dec. 6, 2016

(54) AQUEOUS COMPOSITIONS COMPRISING ARBEKACIN

(75) Inventors: Manfred Keller, Munich (DE); Yukihiro Yagi, Kanagawa (JP); Masashi Tanaka, Kanagawa (JP); Toshie Sugano, Kanagawa (JP); Kuniko Shoji, Kanagawa (JP); Nao Sano, Kanagawa (JP); Michael Hahn, Krailling (DE); Roman Egle, Munich (DE)

(73) Assignees: Meiji Seika Pharma Co., Ltd., Tokyo (JP); PARI Pharma GmbH, Starnberg (DE)

( * ) Notice: Subject to any disclaimer, the term of this patent is extended or adjusted under 35 U.S.C. 154(b) by 26 days.

(21) Appl. No.: 14/344,487

(22) PCT Filed: Aug. 3, 2012

(86) PCT No.: PCT/EP2012/065265
§ 371 (c)(1),
(2), (4) Date: May 29, 2014

(87) PCT Pub. No.: WO2013/037566
PCT Pub. Date: Mar. 21, 2013

(65) Prior Publication Data
US 2014/0343005 A1  Nov. 20, 2014

(30) Foreign Application Priority Data

Sep. 12, 2011  (EP) ..................... 11180927

(51) Int. Cl.
| | |
|---|---|
| A61K 31/7036 | (2006.01) |
| C07H 15/234 | (2006.01) |
| A61K 47/02 | (2006.01) |
| A61K 9/00 | (2006.01) |
| A61K 47/24 | (2006.01) |
| A61K 9/19 | (2006.01) |

(52) U.S. Cl.
CPC ............ *A61K 47/02* (2013.01); *A61K 9/0078* (2013.01); *A61K 9/19* (2013.01); *A61K 31/7036* (2013.01); *A61K 47/24* (2013.01); *C07H 15/234* (2013.01)

(58) Field of Classification Search
None
See application file for complete search history.

(56) References Cited

U.S. PATENT DOCUMENTS

| | | | |
|---|---|---|---|
| 4,029,882 A * | 6/1977 | Wright | C07H 15/236 536/13.6 |
| 5,508,269 A | 4/1996 | Smith et al. | |
| 6,221,388 B1 | 4/2001 | Hersch et al. | |
| 6,987,094 B2 | 1/2006 | Malvolti et al. | |
| 7,718,189 B2 | 5/2010 | Boni et al. | |
| 2007/0071686 A1 | 3/2007 | Lintz et al. | |
| 2007/0218013 A1* | 9/2007 | Baker et al. | 424/46 |
| 2009/0137950 A1 | 5/2009 | Loenner et al. | |
| 2009/0293868 A1 | 12/2009 | Hetzer et al. | |
| 2011/0146670 A1 | 6/2011 | Gallem et al. | |
| 2013/0174840 A1 | 7/2013 | Gallem et al. | |

FOREIGN PATENT DOCUMENTS

| | | |
|---|---|---|
| CN | 101575354 A | 11/2009 |
| EP | 2062608 A2 | 5/2009 |
| JP | 5651499 | 5/1981 |
| JP | 58134099 | 8/1983 |
| JP | 06157580 A | 6/1994 |
| JP | 07082290 A | 3/1995 |
| JP | 07538075 A | 12/2007 |
| WO | 2005037256 A2 | 4/2005 |
| WO | WO-2005/110022 A2 | 11/2005 |
| WO | 2007020073 A1 | 2/2007 |
| WO | 2008043825 A2 | 4/2008 |
| WO | 2009/027095 A1 | 3/2009 |
| WO | 2009135871 A1 | 11/2009 |

OTHER PUBLICATIONS

Narihara, K. et al "The utility of arbekacin in patients . . . " Showa Univ. J. Med. Sci. (1998) vol. 10, No. 1, pp. 69-76.*
RxList entry for sodium chloride injection (2010) http://www.rxlist.com/normal-saline-drug.htm Retrieved Jul. 25, 2015.*
Caplus abstract for Naito, T. et al "Efficacy and pharmokinetics of arbekacin . . . " Chemotherapy (Tokyo) (1994) vol. 42, No. 11, pp. 1254-1258.*
Hamilton-Miller, J. et al "Activitiy of the semi-synthetic kanamycin B derivative . . . " J. Antimicrob. Chem. (1995) vol. 35, pp. 865-868.*
Kawashima Tatsuo et al., "Clinical efficacy of arbekacin on MRSA pneumonia", XP-002667212 & Japanese Journal of Antibiotics, vol. 47, No. 6, pp. 741-750 (1994).
Martindale, "The Complete Drug Reference", 1999, 32nd edition, ed. K. Parfitt Pharmaceutical Press.
Lowry et al., "Effects of pH and osmoloarity on aerosol-induced cough in normal volunteers", Clinical Science, vol. 74, pp. 373-376 (1988).
Eschenbacher et al., "Alteration in Osmolarity of Inhaled Aerosols Cause Bronchocontriction and Cough, but Absence of a Permeant Anion Causes Cough Alone", Am. Rev. Respir. Dis., vol. 129, pp. 211-215 (1984).

(Continued)

*Primary Examiner* — Leigh C Maier
(74) *Attorney, Agent, or Firm* — Mintz Levin Cohn Ferris Glovsky and Popeo, P.C.; Peter F. Corless, Esq.; Daniel W. Clarke

(57) ABSTRACT

The invention provides aqueous liquid pharmaceutical compositions comprising arbekacin and chloride ions. The compositions are well tolerable for use in a method for treatment or prevention of a disease of the upper or lower respiratory tract, wherein the composition is aerosolized and inhaled by the patient. Furthermore, the invention provides arbekacin hydrochloride.

12 Claims, 1 Drawing Sheet

(56) References Cited

OTHER PUBLICATIONS

Weber et al., "Effect of Nebulizer Type and Antibiotic Concentration on Device Performance", Pediatric Pulmonology, vol. 23, pp. 249-260 (1997).
Ratjen et al., "Aminoglycoside therapy against Pseudomonas aeruginosa in cystic fibrosis: A review", Journal of Cystic Fibrosis, vol. 8, pp. 361-369 (2009).
English abstract of Chinese publication CN101575354, Nov. 11, 2009, Beijing University of Chemical Technology.
Ingredient matches for Habekacin; www.drugs.com/international/habekacin.html; 1 page, (2015).
Prescribing information; Description of TOBI®; Novartis Pharmaceuticals Corporation; 16 pages, (2009).
Habekacin injection, 2009, $6^{th}$ edition, pp. 1-6.

* cited by examiner

AQUEOUS COMPOSITIONS COMPRISING ARBEKACIN

CROSS-REFERENCES TO RELATED APPLICATIONS

This application is a 35 U.S.C. §371 U.S. national entry of International Application PCT/EP2012/065265 (WO 2013/037566) having an International filing date of Aug. 3, 2012, which claims under 35 U.S.C. §119 the benefit of European Patent Application No. 11 180 927.3, filed Sep. 12, 2011. The entire contents of both applications are incorporated herein by reference in their entirety.

FIELD OF THE INVENTION

The invention relates to aqueous liquid pharmaceutical compositions comprising arbekacin and chloride ions, which are useful in a method for the treatment or prevention of a disease of the upper or lower respiratory tract. The invention also relates to arbekacin hydrochloride.

BACKGROUND OF THE INVENTION

Aminoglycosides are bactericidal antibiotics derived from bacteria of the order Actinomycetales, more specifically from the genus *Streptomyces* or *Micromonospora*. They are polycationic compounds containing an aminocyclitol with cyclic amino-sugars attached by glycosidic linkages. Generally, the sulfate salts are used. The aminoglycosides have similar toxicological features, with ototoxicity as the major limitation to their use. Other common adverse effects are nephrotoxicity, neuromuscular blocking activity, and allergy, including cross-reactivity. They have a similar antimicrobial spectrum and appear to act by interfering with bacterial protein synthesis, possibly by binding irreversibly to the 30S and to some extent the 50S portions of the bacterial ribosome. They are most active against Gram-negative rods. Gram-negative species including *Brucella, Clymmatobacterium, Campylobacter, Citrobacter, Escherichia, Enterobacter, Klebsiella, Proteus, Providencia, Pseudomonas, Serratia, Vibrio* and *Yersinia* have been reported to be sensitive to aminoglycosides. Furthermore, Gram-positive strains such as *Staphylococcus aureus* are highly sensitive to aminoglycosides such as gentamicin sulfate. Also some actinomycetes and mycoplasmas would be sensitive to aminoglycosides. Bacterial resistance is usually associated with the plasmid-mediated production of inactivating enzymes. Based on their activity spectrum, they are used to treat infections such as biliary-tract infections, brucellosis, cat scratch disease, cystic fibrosis, endocarditis, endometritis, gastro-enteritis, granuloma inguinale, listeriosis, meningitis, otitis externa, otitis media, pelvic inflammatory disease, peritonitis, plague, pneumonia, septicaemia, skin infections and urinary-tract infections, as well as in the prophylaxis of surgical infection and the treatment of immunocompromised patients and those in intensive care. The aminoglycosides have a postantibiotic effect, where the antibacterial activity persists after concentrations have dropped below minimum inhibitory concentrations (Martindale—The complete drug reference, 1999, thirty-second edition, ed. K. Parfitt, Pharmaceutical Press).

Arbekacin is an aminoglycoside derived from dibekacin. It is used as arbekacin sulfate in the treatment of serious infections due to methicillin-resistant *Staphylococcus aureus* (Martindale—The complete drug reference, 1999, thirty-second edition, ed. K. Parfitt, Pharmaceutical Press). Arbekacin was first described in JP 56051499 A and JP 58134099 A and is marketed as an arbekacin sulfate solution for parenteral application.

Little of the aminoglycosides is absorbed from the gastro-intestinal tract, and aminoglycosides have preferably been administered intravenously. However, there is a high potential for severe systemic side effects (such as ototoxicity and nephrotoxicity) due to the narrow margin between therapeutic and toxic doses. Additionally, for treatment of respiratory infections, relatively high parenteral doses must be administered as aminoglycosides diffuse poorly across lipid membranes and into bronchial secretions. This may impair their efficacy as often only sub-inhibitory aminoglycoside concentrations are present at the site of infection. Several approaches to avoid toxicity and increase the efficacy of aminoglycosides have been proposed (Ratjen et al., "Aminoglycoside therapy against *Pseudomonas aeruginosa* in cystic fibrosis: A review", Journal of Cystic Fibrosis 8 (2009) 361-369). For example, U.S. Pat. No. 6,221,388 describes liposome-encapsulated aminoglycoside formulations and U.S. Pat. No. 5,508,269 describes direct administration of tobramycin to the infected respiratory tract.

Aerosolisation of for example gentamicin, tobramycin and amikacin has been evaluated and applied to raise concentrations in the respiratory tract while avoiding toxicity. Examples of aminoglycoside formulations for inhalation are TOBI® (U.S. Pat. No. 5,508,269), Bramitob® (U.S. Pat. No. 6,987,094) and Arikace® (U.S. Pat. No. 7,718,189). However, some of these formulations require very long nebulisation times, which reduce patient compliance.

SUMMARY OF THE INVENTION

The object of the present invention is to provide highly concentrated and well-tolerated arbekacin formulations for inhalation that can be nebulised within a short period of time (i.e. a period of time that is acceptable for patients).

Upon developing a highly concentrated arbekacin formulation for inhalation, the inventors found that the generally used approaches for preparing well-tolerated formulations for inhalation, such as nearly physiologic tonicity, optimised pH and a specific concentration of permeant anions, were not sufficient. Arbekacin formulations prepared according to these approaches caused immediate coughing reactions in healthy volunteers. Therefore, another approach was needed to formulate highly concentrated arbekacin formulations for inhalation.

The inventors surprisingly found that the irritation was related to the sulfate salt form of the arbekacin, although this sulfate form is used in other well-tolerated aminoglycoside formulations for inhalation (e.g. TOBI®, Arikace®). It was found that a certain concentration of chloride ions, completely or partly replacing the sulfate ions in the arbekacin solution, was needed to solve the problem.

Thus, the invention provides an aqueous liquid pharmaceutical composition comprising arbekacin and chloride ions, wherein the concentration of arbekacin, calculated as free base, is at least 100 mg/ml and the ratio of the molar amount of chloride ions to the molar amount of arbekacin is at least 0.9:1.

The composition can be used in a method for the treatment or prevention of a disease of the upper or lower respiratory tract, wherein the method for the treatment or prevention of the disease comprises the step of aerosolizing the composition and letting a patient inhale the aerosol thus produced.

Furthermore, the invention provides a new salt form of arbekacin, namely arbekacin hydrochloride.

DETAILED DESCRIPTION OF THE INVENTION

Figure 1:
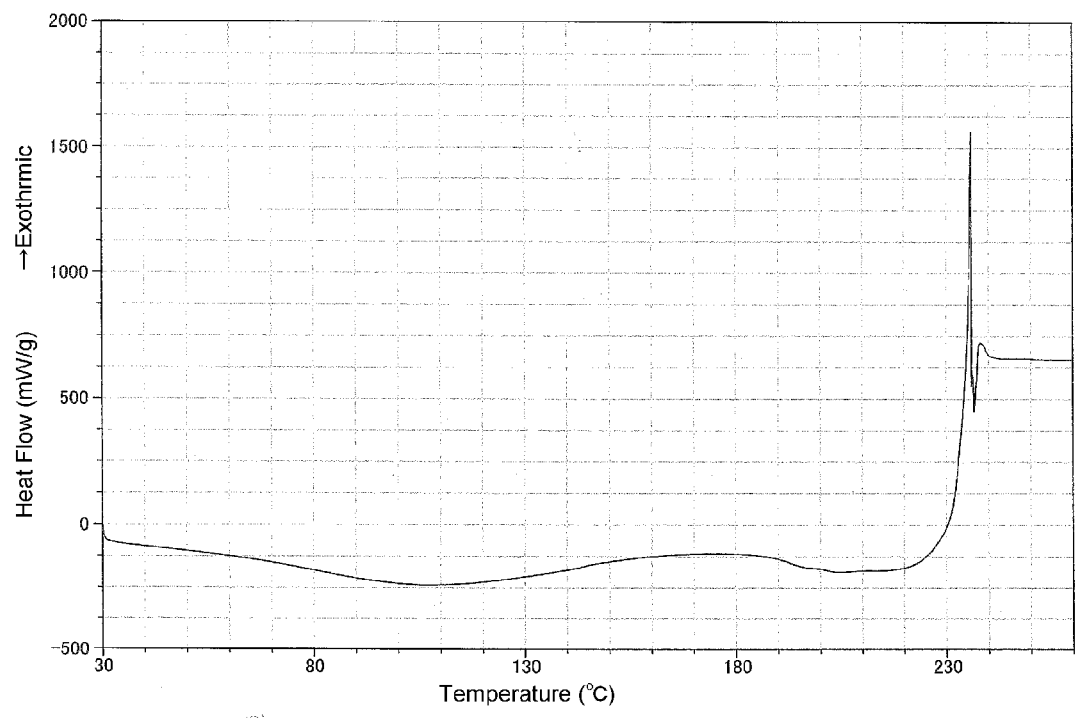
FIG. 1 shows the differential scanning calorimetry curve of arbekacin hydrochloride obtained according to Example 2.

The pharmaceutical compositions according to the invention are aqueous liquids well-suited for administration to the respiratory tract in aerosolized form.

The term composition refers to a mixture of compounds. Synonyms for composition are formulation and preparation. More specifically, the compositions according to the invention are aqueous liquids, i.e. liquid systems wherein the liquid carrier or solvent consists predominantly or completely of water. In specific cases, the liquid carrier can contain small fractions of one or more liquids which are at least partly miscible with water.

The compositions according to the invention are preferably sterile compositions. The term sterility is to be understood in the usual pharmaceutical sense. Several sterilisation methods are available for liquid compositions, such as for example autoclaving and sterile filtration. Sterile filtration is particularly preferred, as this can be implemented in production lines, whereas autoclaving is a batch process.

The active compound of the composition according to the invention is the aminoglycoside antibiotic arbekacin. The composition may be used in a method to prevent or diseases of the upper or lower respiratory tract, especially infections of the upper or lower respiratory tract. Such an infection can be the primary cause of a disease or it can be an infection in cases where an underlying disease of the upper or lower respiratory tract is already present. Examples of such primary and underlying diseases are acute and chronic sinusitis, rhinitis and rhinosinusitis, nasal polyps, nasal furuncles, epistaxis, nasal and sinonasal conditions related to lower respiratory tract diseases such as nasal and sinonasal conditions related to ear diseases such as inflammations of the ear, allergy, oropharyngeal infections, laryngotracheobronchitis, bronchitis, bronchiolitis, such as diffuse bronchiolitis and bronchiolitis obliterans, bronchiectasis, alveolitis, pneumonia such as community acquired pneumonia, hospital acquired pneumonia, ventilator associated pneumonia, healthcare associated pneumonia, aspiration pneumonia, lipid pneumonia, eosinophilic pneumonia, chemical pneumonia, atypic pneumonia and severe acute respiratory system disease, pulmonary infections with or without acute exacerbations, such as bacterial, viral, fungal, and protozoal infections of the respiratory tract, emphysema, sarcoidosis, tuberculosis, nontuberculous mycobacterial pulmonary diseases, parenchymatic and/or fibrotic diseases or disorders including cystic fibrosis and idiopathic pulmonary fibrosis, pulmonary arterial hypertension, interstitial lung diseases, pertussis, and graft rejection after lung, stem cell, or bone marrow transplantation.

Aminoglycoside antibiotics are generally used as the sulfate salt. For all aminoglycosides described in the 32$^{nd}$ edition of Martindale (The complete drug reference, 1999, ed. K. Parfitt, Pharmaceutical Press), it is mentioned that they are used as the sulfate (i.e. amikacin, apramycin, arbekacin, astromicin, capreomycin, dibekacin, dihydrostreptomycin, framycetin, gentamicin, isepamicin, kanamycin, micronomicin, neomycin, netilmicin, paromomycin, ribostamycin, sissomicin, streptomycin and tobramycin). Exceptions are kanamycin, where also acid sulfate salts and the bisulfate are used, neomycin, where mostly sulfate is used but also neomycin undecenoate or hydrochloride are used, and streptomycin, where the sulfate salt is most used but streptomycin hydrochloride also exists.

Arbekacin is only available as its sulfate salt.

In general and inhere, the doses or concentrations of arbekacin are expressed in terms of the free base.

The concentration of arbekacin in the liquid composition of the invention and in the dispersed phase of the aerosol prepared therefrom is at least 100 mg/ml, i.e. relatively high. A high concentration has several advantages in formulations for inhalation, such as easier reaching of the therapeutic concentration at the target site, reduction of the volume needed to be inhaled to reach the therapeutic concentration at the target site and therefore reduction of the nebulization time, longer period of action and therefore reduction of the frequency of application.

The concentration of arbekacin in the liquid composition of the invention and in the dispersed phase of the aerosol prepared therefrom is preferably at least 120 mg/ml, at least 150 mg/ml, at least 200 mg/ml, or at least 250 mg/ml.

In order to be well-tolerated, a pharmaceutical composition for application to the upper and/or lower respiratory tract should, as far as possible, have a physiological tonicity or osmolality. It is known that deviations from this physiological tonicity (about 290 mOsmol/kg, which is the osmolality of physiological fluids), i.e. hypotonic and hypertonic solutions, can induce a cough reflex upon inhalation (Lowry et al., "Effect of pH and osmolarity on aerosol-induced cough in normal volunteers", Clinical Science 74 (1988) 373-376). Furthermore, deviations from physiological tonicity can cause irritation of the surface to which the solutions are applied, as water is either drawn from or into the cells of the surface (when hypertonic solutions or hypotonic solutions, respectively, are applied). However, hypertonic solutions are less irritating than hypotonic solutions and might even have additional advantages in certain respiratory conditions. The main advantage of hypertonic solutions is related to an increased mucus clearance in diseases accompanied with an undesired mucus production. Weber et al. ("Effect of nebuliser type and antibiotic concentration on device performance", Paediatric Pulmonology 23 (1997) 249-260) suggest that the optimal osmolality for inhaled antibiotic solutions lies between 150 and 550 mOsmol/kg.

Additional suggestions from literature for reducing cough and bronchoconstriction upon aerosol inhalation, are an optimal pH, being larger than 2.6 and smaller than 10.0 (Lowry et al., "Effect of pH and osmolarity on aerosol-induced cough in normal volunteers", Clinical Science 74 (1988) 373-376), and the presence of permeant anions in a concentration between 31 and 300 mM (Weber et al. "Effect of nebuliser type and antibiotic concentration on device performance", Paediatric Pulmonology 23 (1997) 249-260; Eschenbacher et al., "Alteration in osmolarity of inhaled aerosols cause bronchoconstriction and cough, but absence of a permeant anion causes cough alone", Am. Rev. Respir. Dis. 129 (1984) 211-215).

The inventors of the present invention found that inhalation of highly concentrated solutions of arbekacin sulfate with a pH of about 7.0, a nearly physiological tonicity of about 300 to about 380 mOsmol/kg, and with NaCl added to provide the permeant anion (about 34 to about 46 mM)

induced serious and immediate coughing, despite being optimised according to the state of the art to prevent cough reactions. Similar cough responses and bronchoconstriction have been found when inhaling tobramycin sulfate solutions with preservatives such as phenol and sodium metabisulfite. However, the tested arbekacin sulfate formulations did not contain preservatives or excipients that are known to cause a cough response or bronchoconstriction.

Further to omitting preservatives and other critical excipients from the formulations, it was suggested to improve tolerability of, for example, tobramycin formulations by reducing the concentration of sodium chloride (e.g. quarter strength saline instead of full strength saline) or even omit sodium chloride from the formulation, as described in U.S. Pat. No. 5,508,269, U.S. Pat. No. 6,987,094, and WO 2005/037256. However, although the composition, and also the sodium chloride concentration, of the formulations tested by the inventors of the present invention was close to the composition of marketed aminoglycoside formulations for inhalation, which are generally well tolerated (TOBI®), the tested highly concentrated arbekacin solutions still caused an immediate coughing reaction.

In summary, the solutions suggested in the prior art to formulate a well-tolerable arbekacin composition for inhalation were found not to be sufficient.

However, the inventors found that the irritation of these highly concentrated formulations was related to the sulfate salt form of arbekacin. This was unexpected, especially as the known aminoglycoside formulations for inhalation contain the sulfate salt of the aminoglycoside (e.g. TOBI®, Arikace®). However, when using arbekacin base instead of the commercially available arbekacin sulfate, and hydrochloric acid to adjust pH, a highly concentrated arbekacin solution was obtained that could be inhaled without coughing reactions. This arbekacin hydrochloride formulation showed a much higher osmolality than its sulfate salt counterpart and more than the in prior art advised concentration of permeant anions, but despite this, the formulation was well tolerated upon inhalation. No cough reaction or bronchoconstriction was induced, as was shown in a guinea pig model and human volunteers.

More specifically, the inventors found that a minimal concentration of chloride ions was needed in the formulation. Different formulations were prepared from arbekacin base using either hydrochloric acid or sulphuric acid or both for pH adjustment. A formulation with the ratio of the molar amount of chloride ions to the molar amount of arbekacin being 0.16:1 induced immediate coughing, whereas formulations wherein this ratio was increased to at least 0.9:1 were much better tolerated.

Thus, the ratio of the molar amount of chloride ions to the molar amount of arbekacin in the composition according to the invention is at least 0.9:1. Preferably, this ratio is at least 3:1 and more preferably, at least 5:1.

Even formulations with a very high ratio of the molar amount of chloride ions to the molar amount of arbekacin, and therefore also a very high osmolality, were better tolerated upon inhalation than the formulations where this ratio was less than 0.9:1.

In another aspect, it was found useful to reduce the amount of sulfate ions in highly concentrated arbekacin solutions for inhalation.

Thus, the molar amount of sulfate ions in the aqueous liquid pharmaceutical composition according to the invention is preferably no greater than 200 mol-% of the molar amount of arbekacin. More preferably, the molar amount of sulfate ions in the aqueous liquid pharmaceutical composition according to the invention is no greater than 50 mol-% of the molar amount of arbekacin. Even more preferably, the composition is substantially free of sulfate ions. i.e. it contains sulfate ions only as unavoidable impurities.

Furthermore, the inventors have prepared, for the first time, a solid arbekacin hydrochloride by freeze-drying. As evaluated by differential scanning calorimetry and thermal gravimetric analysis, an amorphous solid was obtained. The drug compound was characterised by an optical rotation $[\alpha]^{20}_D$ of +79.8°. Additionally, the structural formula and position numbers were analysed by nuclear magnetic resonance. Also, ion chromatography was used to determine the chloride content in the arbekacin hydrochloride solid. It was found that the drug compound contained 19.66% chloride, corresponding to a chloride number of approximately 3.5 to 4.0.

Thus, the invention also provides (solid) arbekacin hydrochloride. This new compound is useful in the preparation of the aqueous liquid pharmaceutical composition according to the invention.

The arbekacin hydrochloride may be prepared by a method comprising the following steps: (1) arbekacin free base is dissolved in distilled water (preferably at a concentration of about 0.5 mol/l); (2) the pH of the solution is adjusted to about 7 by adding aqueous hydrochloric acid solution (preferably having a concentration of about 6 mol/l); (3) the resulting solution may optionally be diluted with distilled water (preferably about 0.5 litres per mole of arbekacin); (4) the solution is then subjected to freeze-drying to obtain arbekacin hydrochloride.

As hyperosmotic arbekacin hydrochloride compositions were shown to be well tolerable upon inhalation, the osmolality of the liquid composition of the invention can be increased above the generally accepted maximal tolerable level. The osmolality composition is preferably at least 350 mOsmol/kg and more preferably, the osmolality is in the range of 550 mOsmol/kg to 1500 mOsmol/kg. Furthermore, the osmolality can range between 800 mOsmol/kg and 1500 mOsmol/kg and between 1000 mOsmol/kg and 1500 mOsmol/kg.

The pharmaceutical composition can contain excipients such as tonicity-adjusting excipients, excipients for adjusting or buffering the pH, antioxidants, surfactants, excipients for sustained release or prolonged local retention, taste-masking agents, sweeteners, and flavours. These excipients are used to obtain an optimal pH, viscosity, surface tension and taste, which support the formulation stability, the aerosolization, the tolerability and/or the efficacy of the formulation upon inhalation.

When necessary, tonicity-adjusting excipients can be additionally incorporated in the compositions of the invention. As used herein, a tonicity-adjusting component or excipient is understood as one or more pharmaceutical excipients which are osmotically active and which are used in common practice for the purpose of adjusting the osmolality or tonicity of liquid pharmaceutical formulations. Commonly used examples of such excipients are sodium chloride and mannitol. Other salts that can be used for adjusting tonicity are sodium gluconate, sodium pyruvate, and potassium chloride. Also carbohydrates can be used for this purpose. Examples are sugars such as glucose, lactose, sucrose and trehalose, and further sugar alcohols such as xylitol, sorbitol, and isomaltol.

Preferably, the liquid composition of the invention contains sodium chloride. Preferably, the concentration of sodium chloride is 1 to 5 g/l, more preferably 2 to 3 g/l, more preferably about 2.5 g/l.

The inventors found that the pH of the aqueous liquid pharmaceutical composition should preferably lie in the slightly acidic to neutral region, i.e. the composition preferably has a pH ranging between about 3 to about 7. A pH in the range of about 5 to about 7 is particularly preferred. The acidic pH was found to help preventing the discolouration that is often seen upon storage of aminoglycoside solutions.

The composition can comprise one or more excipients to adjust and/or buffer the pH value of the solution. For adjusting and optionally buffering pH, physiologically acceptable acids, bases, salts, and combinations thereof may be used. Excipients often used for lowering the pH value or for application as acidic component in a buffer system are strong mineral acids, in particular sulfuric acid and hydrochloric acid. In the current invention, it is especially preferred to use hydrochloric acid to adjust pH, which then forms arbekacin hydrochloride salt in situ. However, also inorganic and organic acids of medium strength as well as acidic salts may be used, such as, for example, phosphoric acid, citric acid, tartaric acid, succinic acid, fumaric acid, methionine, acidic hydrogen phosphates with sodium or potassium, lactic acid, and glucuronic acid. Excipients suitable for raising the pH or as basic component in a buffer system are, in particular, mineral bases such as sodium hydroxide or other alkali and alkaline earth hydroxides and oxides such as, for example, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, and citrates such as sodium citrate.

The composition can also comprise a buffer system consisting of two components. One of the most preferred buffer systems contains citric acid and sodium citrate. Nevertheless, other buffering systems may also be used.

Antioxidants are natural or synthetic substances which prevent or interrupt the oxidation of active agents and/or oxidative injury in stressed tissues and cells. Antioxidants can be adjuvants which are oxidisable themselves (i.e. primary antioxidants) or adjuvants that act as reducing agents (i.e. reducing antioxidants), such as, for example, tocopherol acetate, lycopene, reduced glutathione, catalase, and peroxide dismutase. Other adjuvants used to prevent oxidative reactions are synergistic antioxidants, which do not directly act in oxidation processes, but indirectly via the complexation of metal ions that are known to catalyse oxidation reactions. Frequently used synergistic antioxidants are ethylenediamine tetraacetic acid (EDTA) and its derivatives. Further useful antioxidants (primary, reducing and/or synergistic anti-oxidising working mechanism) are ascorbic acid and its salts, esters of ascorbic acid, fumaric acid and its salts, malic acid and its salts, citric acid and its salts, butyl hydroxy anisole, butyl hydroxy toluene, propyl gallate, and maltol. As an alternative to generally used antioxidants, substances such as acetylcysteine, R-cysteine, vitamin E TPGS, pyruvic acid and its magnesium and sodium salts, and gluconic acid and its magnesium and sodium salts, might also be useful in formulations for inhalation. The salts of gluconic acid have the additional advantage that they have been described to have an anti-oxidising effect on stressed tissues and cells, which can be particularly advantageous in the treatment of inflammations, as oxygen radicals induce and perpetuate inflammatory processes. Also pyruvate salts are believed to have such in vivo anti-oxidising effects.

Preferably the liquid composition according to the invention contains ethylenediamine tetraacetic acid sodium salt (Na-EDTA). Preferably the concentration of Na-EDTA is 0.01% to 0.5% by weight, more preferably about 0.02% by weight.

An additional measure to prevent oxidation and to contribute to the prevention of the undesired discolouration is the replacement of oxygen above the solution by an inert gas such as nitrogen or argon.

Furthermore, the surface tension of a liquid composition is important for optimal nebulization. The surface tension should range between about 25 and 80 mN/m, and more preferably between 30 to 75 mN/m. Compositions with a surface tension in the lower part of this range are expected to show a good spreadability on the mucous membranes of the respiratory tract. Furthermore, the surface tension might need to be adjusted to allow a good emptying of the composition from its primary package, which might be particularly important since highly concentrated aminoglycoside formulations may be sticky due to their sugar nature.

Surface-active materials (or surfactants) can be included to adjust the surface tension for the above described reasons, and further for stabilization, taste-masking and/or sustained release. Another advantage of surface-active excipients is that they can improve the permeability of arbekacin into bacterial cells resulting in a more pronounced antibacterial activity. Additionally, it is suggested in the literature that surfactants may help to disrupt or disperse biofilms formed by bacteria and fungi, thereby improving the antibacterial efficacy of arbekacin against mucoid bacteria forms.

Surfactants are materials with at least one relatively hydrophilic and at least one relatively lipophilic molecular region that accumulate at hydrophilic-lipophilic phase interfaces and reduce the surface tension. The surface-active materials can be ionic or non-ionic. Particularly preferred surfactants are those that have a good physiological compatibility and that are considered safe for oral or nasal inhalation. Preferred surfactants are, for example, tyloxapol, polysorbates, such as polysorbate 80, lecithin, vitamin E TPGS, and macrogol hydroxystearates, such as macrogol-15-hydroxystearate. The surfactant component might also comprise a mixture of two or more surfactants, such as polysorbate 80 in combination with vitamin E TPGS.

The total content of the surfactant component in solutions for application to the respiratory tract should be limited to a maximum of about 5% (w/v) in order to avoid mucosal irritation. Particularly preferred concentrations are between about 0.01 to about 2.0% (w/v), and between about 0.02 to about 1% (w/v).

Preferably, the liquid composition of the invention contains 0.01 to 0.5% (w/v), more preferably 0.03 to 0.1% (w/v) of polysorbate 80, lecithin or vitamin E TPGS.

In some of the embodiments of the invention, also taste-masking agents will be useful excipients. A bad taste of formulations for inhalation is extremely unpleasant and irritating. The bad taste sensation upon inhalation results from direct deposition of aerosol droplets in the oral and pharyngeal region upon oral inhalation, from transport of drug from the nose to the mouth upon nasal inhalation, and from transport of the drug from the respiratory tract to the mouth related to the mucociliary clearance in the respiratory system. As used herein, a taste-masking agent is any pharmaceutically acceptable compound or mixture of compounds capable of improving the taste of an aqueous system, regardless of the mechanism by which the improvement is brought about. For example, the taste-masking agent may cover the poor taste, i.e. reduce the intensity by which it is perceived, or it may correct the taste by adding another, typically more pleasant, flavour to the composition, thereby improving the total organoleptic impression. Other taste-masking mechanisms are complexation, encapsulation, embedding or any other interaction between drug and other compounds of the composition.

The taste-masking agent can be selected from the group of pharmaceutically acceptable sweeteners, such as, for example, saccharin, aspartame, cyclamate, sucralose, acesulfame, neotame, thaumatin, and neohesperidine, including salts and solvates thereof, such as, for example, the sodium salt of saccharin and the potassium salt of acesulfame. Furthermore, sugars such as sucrose, trehalose, fructose, and lactose, or sugar alcohols, such as xylitol, mannitol, and isomalt can be used. Further useful taste-masking agents include pharmaceutically acceptable surfactants, alkali or alkaline earth metal salts, organic acids, such as citric acid and lactic acid, and amino acids, such as arginine. Also aromatic flavours, such as the ingredients of essential oils (such as menthol, thymol and cineol) may be used to improve the taste and tolerability of the composition according to the invention.

In certain embodiments, excipients can be added that increase the adherence of the composition according to the invention to the mucosal surfaces of the respiratory tract. This can for example contribute to an increased residence time of the composition on the site of application and an improved efficacy of the drug. Such excipients can be mucoadhesive excipients, viscosity increasing excipients, and/or gel-forming agents. Examples are polymers such as polyvinylpyrrolidone, dextrans, modified starches, chitosan, carbomers and cellulose derivatives such as hydroxypropylmethylcellulose and viscous liquids such as propylene glycol and glycerol.

Further excipients can be added for their advantageous effect on the respiratory tract. For example, a magnesium salt such as magnesium gluconate can be added. Magnesium is known to increase the enzymatic activity of Dornase alpha, an enzyme that reduces mucus viscosity. This is especially useful in bacterial infection and inflammation as the respiratory mucus then becomes more viscous and purulent. In addition, the low permeability of the gluconate anion may facilitate mucociliary clearance. Furthermore, magnesium gluconate may have a cytoprotective and biological anti-oxidising effect.

Preferably, the composition according to the invention is formulated as a molecular solution of arbekacin. However, the active agent (arbekacin) can also be colloidally dispersed in the aqueous liquid. Colloidal carrier systems, such as micelles, mixed micelles, colloidal complexes, and liposomes, can be useful for the targeted delivery of the active agent.

According to a further aspect of the invention, the pharmaceutical compositions according to the invention are used in a method for treatment or prevention of a disease of the upper or lower respiratory tract. Such diseases are, in particular, caused by or related to bacterial infections, where the bacteria are susceptible to arbekacin.

The method for the treatment or prevention of the disease comprises the step of aerosolizing the composition and letting a patient inhale the aerosol thus produced. An aerosol is defined herein as a system comprising a continuous gas phase and, dispersed therein, a discontinuous or dispersed phase of liquid and/or solid particles. Aerosols comprising a dispersed liquid phase and a continuous gas phase are sometimes referred to as "liquid aerosols" or, probably more appropriately, "aerosolized liquids".

In this embodiment, the dispersed phase essentially consists of liquid droplets. The droplets of the dispersed phase comprise arbekacin in a liquid environment. The liquid environment is mainly an aqueous phase, with or without further excipients as described above. Preferably, the liquid phase contains arbekacin in a molecular solution or colloidal dispersion. It will be understood by the person skilled in the art, that the features and preferences with respect to the liquid composition, as disclosed herein-above, may also be applied to the dispersed phase of the aerosol generated therefrom and vice versa.

The continuous gas phase of the aerosol may be selected from any gas or mixture of gases which is pharmaceutically acceptable. For example, the gas may simply be air or compressed air, which is most common in inhalation therapy using nebulizers as aerosol generators. Alternatively, other gases and gas mixtures, such as air enriched with oxygen, carbon dioxide, or mixtures of nitrogen and oxygen may be used.

The dispersed phase of the aerosol prepared from the compositions of the invention exhibits a mass median aerodynamic diameter (MMAD) preferably from about 1 to about 6 µm and more preferably from about 2 to about 4.5 µm or from about 1.5 to about 4 µm. The MMAD is measured using cascade impaction methods for liquid aerosols and describes the diameter below which 50% of the aerosolized drug mass is contained, in other words, 50% of the drug mass is contained in droplets having a diameter smaller than the MMAD.

Another parameter describing the dispersed phase of the aerosol is the particle size distribution of the aerosolized liquid particles or droplets. The geometric standard deviation (GSD) is an often used measure for the broadness of the particle or droplet size distribution of generated aerosol particles or droplets.

The selection of the precise MMAD within the above described range should take the target region or tissue for deposition of the aerosol into account. For example, the optimal droplet diameter will differ depending on whether oral or nasal inhalation is intended, and whether oropharyngeal, bronchial, pulmonary, nasal, and/or paranasal sinus delivery is focussed upon. Additionally, the age of the patients and their breathing pattern belong to the important factors determining the optimal particle size for drug delivery to the lungs.

For the treatment of the upper airways, in particular the sinonasal mucosa, osteomeatal complex, and paranasal cavities, an MMAD in the range from 2.0 to 4.5 µm is particularly suitable.

If the aerosol is intended for pulmonary delivery, it preferably has an MMAD below 5.0 µm. Preferably, the MMAD is in the range from about 2.0 to about 4.5 µm and a GSD in the range from about 1.2 to about 2.2, preferably from about 1.2 to about 1.8, or more preferably, from about 1.4 to about 1.6. Such particle size and particle size distribution parameters are particularly useful to achieve a high local drug concentration in the lungs, including the bronchi and bronchioli, relative to the amount of drug which is aerosolized. In this context it must be considered that deep lung deposition requires smaller MMADs than deposition in the central airways and that for babies and younger children smaller droplet sizes in the range from about 1.5 to about 3 µm are more preferred.

The aerosol can be generated with any conventional aerosol generator. As used herein, an aerosol generator is a device or a combination of devices capable of generating and emitting an aerosol. According to the present invention, the device is capable of aerosolizing a liquid material into a dispersed liquid phase. Typically, such device is referred to as a nebulizer. Depending on the type and model of the device, the aerosol generator of the invention may require or include a compressor. In other words, the term aerosol generator is used for the complete apparatus or assembly required to produce and emit an aerosol and to administer the aerosol to an animal or to a human patient. Preferably, the nebulizer is selected from jet, ultrasonic, piezoelectric, jet collision, electrohydrodynamic, capillary force, perforated membrane, or perforated vibrating membrane nebulizers.

A preferred aerosol generator for application of an aerosol in the upper respiratory tract is a nebulizer generating the aerosol via a perforated vibrating membrane principle, such as the device known as eFlow®, but which is also capable of emitting a pulsating aerosol. This type of nebulizer has a nose piece for directing the aerosol flow into the nose. Aerosols generated by such a modified electronic nebulizer can reach sinonasal or paranasal cavities much better than when the aerosol is generated in a continuous mode. The pulsating pressure waves achieve a more intensive ventilation of the sinuses so that a concomitantly applied aerosol is better distributed in these cavities. Examples for such electronic nebulization devices are disclosed in WO 2009/027095.

If the intended use is the delivery of the active agent (i.e. arbekacin) to an affected (or potentially affected) site of the lower airways such as the bronchi or the deep lungs, it is particularly preferred that a piezoelectric, electro-hydrodynamic, or perforated membrane-type nebulizer is selected for generating the aerosol. Examples of suitable nebulizers include the I-Neb®, Micro Air®, Multisonic®, Respimate®, eFlow®, AeroNeb®, AeroNeb Pro®, and AeroDose® device families. A particularly preferred nebulizer for targeting the drug to the lower respiratory tact is the eFlow® electronic vibrating membrane nebulizer.

Another preferred nebulizer concept is the investigational eFlow® Closed System as described in WO 2007/020073. This system is an adapted vibrating membrane nebulizer wherein an ampoule containing a drug solution can be inserted in the closing cap of the nebulizer reservoir. The ampoule, as described in EP 2 062 608, is only opened when the nebulizer cap is closed by an opening system incorporated in the nebulizer. This allows the drug solution to immediately flow in the nebulizer reservoir, thereby leading to a more reproducible and accurate dosing associated with reduced aerosol losses.

A particularly preferred nebuliser concept for applying arbekacin according to the invention is a perforated vibrating membrane nebuliser that is designed to be placed in the tubing circuit of a ventilator system in a hospital environment. Such nebulisers are described in WO 2009/135871. The nebulisation of the arbekacin compositions of the invention with such a nebuliser system is particularly advantageous for treatment of, for example, hospital acquired pneumonia, community acquired pneumonia, ventilator associated pneumonia (HAP, CAP, VAP) and other respiratory diseases which require treatment in a hospital.

Whether adapted for pulmonary or sinonasal delivery, the nebulizer should preferably be selected or adapted to be capable of aerosolizing a unit dose at a preferred output rate. A unit dose is defined herein as a volume of the liquid composition comprising the effective amount of active compound designated to be administered during a single administration. Preferably, the nebulizer can deliver such a unit dose at a rate of at least about 0.1 ml/min or, assuming that the relative density of the composition will normally be around 1, at a rate of at least about 100 mg/min. More preferably, the nebulizer is capable of generating an output rate of at least about 0.15 ml/min or 150 mg/min, respectively. In further embodiments, the output rates of the nebulizer are at least about 0.2, 0.3, 0.4, 0.5, 0.6, 0.7, 0.8, 0.9 or 1 ml/min.

Furthermore, the output rate of the nebulizer should be selected to achieve a short nebulization time of the liquid composition. Obviously, the nebulization time will depend on the volume of the composition which is to be aerosolized and on the output rate. Preferably, the nebulizer should be selected or adapted to be capable of aerosolizing a volume of the liquid composition comprising an effective dose of the active compound within not more than about 20 minutes. More preferably, the nebulization time for a unit dose is not more than about 10 minutes. In a further embodiment, the nebulizer is selected or adapted to enable a nebulization time per unit dose of not more than about 6 minutes, and more preferably not more than about 3 minutes. Presently most preferred is a nebulization time in the range from about 0.5 to about 3 minutes.

The volume of the formulations is preferably low in order to allow short nebulization times. The volume, also referred to as the volume of a dose, or a dose unit volume, or a unit dose volume, should be understood as the volume which is intended for being used for one single administration. Specifically, the volume may be in the range from about 0.3 to about 3.5 ml, preferably about 0.4 to about 3.5 ml. In case a residual volume is desired or helpful, this residual volume should be less than 1 ml, more preferably less than 0.5 ml, and most preferably less than 0.2 ml. The effectively nebulized volume is then preferably in the range from about 0.1 to about 2.5 ml or about 0.25 to about 2.5 ml, or more preferably in a range from about 0.2 to about 1.5 ml or about 0.5 to about 1.5 ml.

For specific embodiments of the invention, a method for preparing the aqueous liquid composition defined hereinabove is provided. The method comprises the steps of (a) providing the ingredients of the composition; (b) combining the ingredients provided in step (a) to form an aqueous liquid composition; (c) sterile filtration of the composition obtained in step (b); and (d) filling the sterile filtered composition obtained in step (c) into sterile containers under aseptic conditions. The steps (a) to (d) are conducted in this sequence. Optionally, the method may include further steps, and each of the steps (a) to (d) may comprise a number of substeps.

It is advisable to saturate all solutions with an inert gas such as nitrogen to expel oxygen to avoid degeneration of arbekacin which is typically associated with a colorization of the solution.

Subsequently, sterile filtration of the resulting aqueous solution is conducted. How to select an appropriate filter and conduct the sterile filtration process is per se known to a person skilled in the art. Typically, one or two filtrations through filters having a pore size of 0.22 µm, optionally with a pre-filter with a pore size of 0.45 µm, are recommended.

The subsequent filling of the sterile solution into the final containers is performed under aseptic conditions in an inert gas saturated atmosphere. Pre-sterilised glass vials may be selected as containers. More preferably, sterile plastic vials which are manufactured inline using a blow-fill-seal process design are used, in particular if the product is packaged as single dose units with a dose volume in the range from about 0.2 to about 5 ml. Alternatively, blisters made of aluminium or aluminium coated polymers or other suitable polymeric material mixtures may be used as packaging material for a unit dose application allowing an aseptic filling of the liquid drug formulation.

Blow-fill-seal vials may be formed in a bottle shaped design with a closure which can be removed by twisting or bending. The thus formed opening allows a dropwise dosing and entire emptying, meeting a dispensing uniformity as claimed by Pharmacopoeias. The opening may further be designed such that it fits onto a luer connection or luer lock connection. In this way, a common syringe with luer connection could be connected tightly to the container, for example, in order to take up the contents of the container and transfer it to a nebulizer.

Even more preferred, the blow-fill-seal vial may be designed so that it may be connected essentially tightly with a connection piece of a correspondingly adapted nebulizer, whereby it is possible to fill the preparation directly into the reservoir of the inhaler as described in EP 2 062 608. An example for such an adapted nebulizer is the investigational eFlow® Closed System perforated vibrating membrane nebulizer. The vial is placed in the cover lid of the nebulizer reservoir and pierced by fitting the cover lid on the nebulizer. This system ensures that no drug will be spilled when filled into the medication cup of a nebulizer and the recommended dose will be dispensed as claimed in the medication label.

One or more primary packaging means may be packaged in one secondary packaging means, such as a cardboard box.

The following examples serve to illustrate the invention; however, these are not to be understood as restricting the scope of the invention.

EXAMPLES

Example 1

100 and 150 mg/ml Arbekacin Solutions Based on Arbekacin Sulfate (not According to the Invention)

A solution of 100 mg/ml arbekacin (used as its sulfate salt) containing 0.02% Na-EDTA as stabilizer was prepared. The pH was adjusted with sulfuric acid and its osmolality was adjusted by adding sodium chloride. Additionally, a 150 mg/ml arbekacin formulation (with arbekacin used as its sulfate salt), also containing 0.02% Na-EDTA as stabilizer, was prepared. The formulations were sterile filtered and filled in glass vials. The arbekacin concentration of both formulations was expressed as the concentration of the base. The composition of the formulations is shown in Table 1. The ratio of the molar amount of chloride ions to the molar amount of arbekacin is also shown in Table 1. The physicochemical parameters are shown in Table 2. This example is for comparison.

TABLE 1

Composition of arbekacin sulfate solutions with ratio of molar amount of chloride ions to the molar amount of arbekacin (Ratio Cl:ABK)

|  | Arbekacin 100 mg/ml | Arbekacin 150 mg/ml |
| --- | --- | --- |
| Arbekacin sulfate | 14 g | 21 g |
| Na-EDTA | 0.02 g | 0.02 g |
| NaCl | 0.27 g | 0.20 g |
| $H_2SO_4$ 1 N | q.s. ad pH 7 | q.s. ad pH 7 |
| Aqua purificata | ad 100 ml | ad 100 ml |
| Ratio Cl:ABK | 0.25:1 | 0.13:1 |

TABLE 2

Physicochemical parameters of arbekacin sulfate solutions

|  | Arbekacin 100 mg/ml | Arbekacin 150 mg/ml |
| --- | --- | --- |
| pH (after adjustment) | 7.17 | 7.12 |
| Osmolality [mOsmol/kg] | 299 | 378 |
| Viscosity [mPa•s] | 1.69 | 2.32 |
| Density [g/cm$^3$] | 1.0645 | 1.0961 |
| Surface tension [mN/m] | 72.27 | 72.49 |
| Optical appearance | Clear solution, free of particles | Clear solution, free of particles |

The aerosol performance of both formulations was evaluated with an investigational eFlow® Inline system. The Mass Median Diameter (MMD) and the particle size distribution (Geometric Standard Deviation—GSD) as well as the Total Output Rate (TOR) were measured. The particle size parameters were measured by laser diffraction. Results are shown in Table 3.

TABLE 3

Aerosol performance of arbekacin sulfate solutions

| Arbekacin formulation | MMD [μm] | GSD | TOR [mg/min] | % <5 μm | % <3.33 μm |
| --- | --- | --- | --- | --- | --- |
| 100 mg/ml | 2.96 | 1.48 | 396 | 89.70 | 59.93 |
| 150 mg/ml | 2.86 | 1.42 | 319 | 94.59 | 66.42 |

Upon inhalation, both formulations induced cough. However, diluting the formulations to a concentration of only 50 mg/ml arbekacin resulted in a formulation that was better tolerated upon inhalation.

Example 2

Preparation and Analysis of Arbekacin Hydrochloride 3.0 g (5.36 mmol) of arbekacin free base (potency 988 μg/mg) was dissolved in 11 ml of distilled water and the pH of the solution was adjusted to about 7.0 by adding 6 mol/l aqueous hydrochloric acid solution. The resulting solution was diluted by adding 3 ml of distilled water and was then subjected to freeze drying, resulting in 3.82 g of solid arbekacin hydrochloride.

The following analyses were carried out:

A DSC (Differential Scanning calorimetry) scan was recorded in a crimping pan made of aluminium under an atmosphere of $N_2$ at a gas flow rate of 50 ml/min over the temperature range of 30° C. to 280° C. at a heating rate of 5° C./min. The result is shown in FIG. 1. No clear endothermic peaks were observed in the DSC scan, which indicates that the arbekacin hydrochloride was an amorphous solid.

Figure 2:
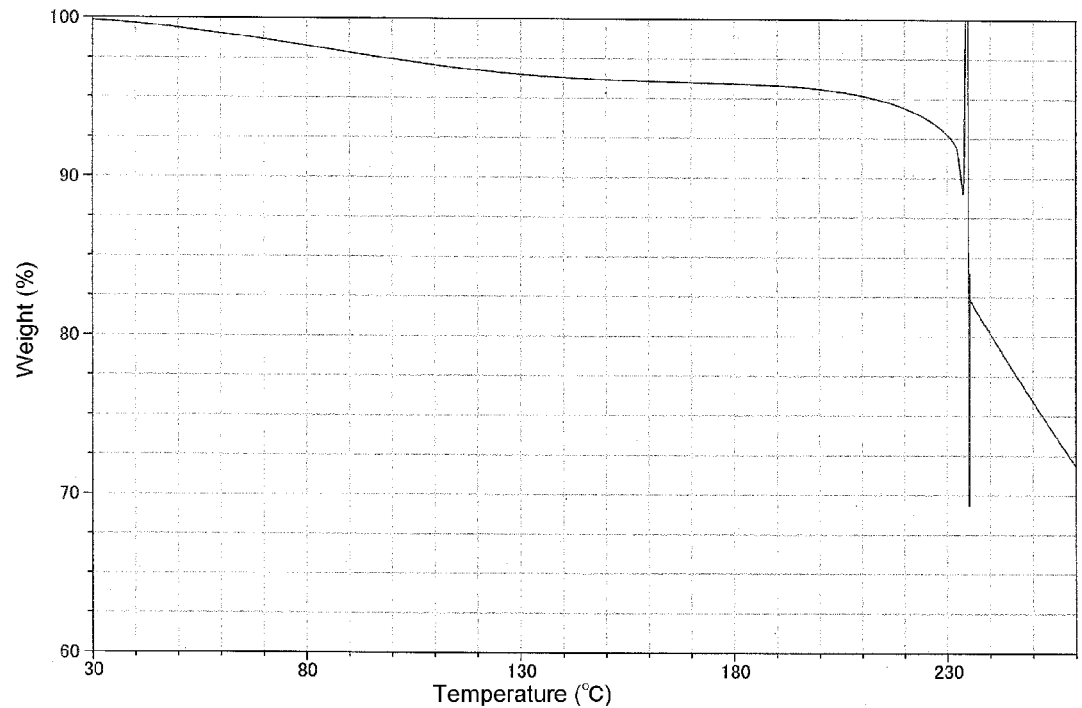
FIG. 2 shows the thermal gravimetric analysis curve of arbekacin hydrochloride obtained according to Example 2.

A TGA (Thermal Gravimetric Analysis) scan was recorded in an open pan made of platinum under an atmosphere of $N_2$ at a gas flow rate of 60 ml/min over the temperature range of 30° C. to 280° C. at a heating rate of 5° C./min. The result is shown in FIG. 2.

$^1$H and $^{13}$C NMR (Nuclear Magnetic Resonance) spectra were recorded on a solution in deuterium oxide at a concentration of 30 mg/m using 3-(trimethylsilyl) propionic acid-$d_4$ sodium salt as internal reference compound. The signals observed and their assignment based on the position numbers shown in the following structural formula are summarized in Tables 4 and 5, respectively.

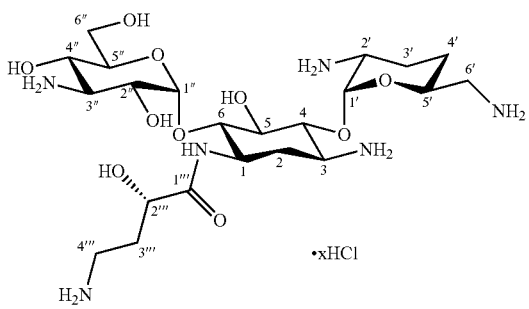

TABLE 4

Assignment of $^1$H-NMR spectrum of arbekacin hydrochloride

| δ (ppm) | Intensity | Multiplicity | Assignment |
|---|---|---|---|
| 1.61 | 1H | m | 4'a |
| 1.70 | 1H | ddd (J = 12.7, 12.7, 12.7 Hz) | 2a |
| 1.91-2.07 | 4H | m | 3', 3'''a, 4'b |
| 2.13 | 1H | m | 2b |
| 2.18 | 1H | m | 3'''b |
| 3.10 | 1H | dd (J = 7.7, 13.4 Hz) | 6'a |
| 3.19 | 2H | dd (J = 7.3, 7.3 Hz) | 4''' |
| 3.25 | 1H | dd (J = 3.3, 13.4 Hz) | 6'b |
| 3.28 | 1H | m | 3 |
| 3.39 | 1H | dd (J = 10.3, 10.3 Hz) | 3'' |
| 3.54 | 1H | m | 2' |
| 3.67 | 1H | dd (J = 10.3, 10.3 Hz) | 4'' |
| 3.74-3.88 | 6H | m | 2'', 4, 5, 6, 6'' |
| 4.03 | 1H | m | 5'' |
| 4.09 | 1H | m | 1 |
| 4.23 | 1H | m | 5' |
| 4.29 | 1H | dd (J = 3.8, 9.3 Hz) | 2''' |
| 5.18 | 1H | d (J = 3.8 Hz) | 1'' |
| 5.73 | 1H | d (J = 3.5 Hz) | 1' |

TABLE 5

Assignment of $^{13}$C-NMR spectrum of arbekacin hydrochloride

| δ (ppm) | Assignment | δ (ppm) | Assignment | δ (ppm) | Assignment |
|---|---|---|---|---|---|
| 20.9 | 3' | 49.1 | 1 | 75.1 | 5 |
| 25.7 | 4' | 55.0 | 3'' | 80.0 | 4 |
| 30.8 | 3''' | 59.8 | 6'' | 80.6 | 6 |
| 32.2 | 2 | 65.7 | 5' | 95.1 | 1' |
| 37.0 | 4''' | 65.9 | 4'' | 98.0 | 1'' |
| 42.7 | 6' | 68.3 | 2'' | 175.4 | 1''' |
| 48.9 | 2' | 69.6 | 2''' | | |
| 48.9 | 3 | 72.1 | 5'' | | |

The Optical rotation $[\alpha]^{20}_D$ was determined according to Japanese Pharmacopoeia (Section 2.49) (after drying, 0.25 g/water 25 ml, 100 mm). As shown in Table 6, the optical rotation $[\alpha]^{20}_D$ of arbekacin hydrochloride was +79.8°.

TABLE 6

Results of optical rotation measurements

| | Run 1 | Run 2 | Run 3 | Average | Reported value |
|---|---|---|---|---|---|
| Optical rotation $[\alpha]^{20}_D$ | +80.2° | +79.6° | +79.6° | +79.8° | +80° |

An assay for chloride by ion chromatography was carried out under the following conditions: Sample solution: 7 mg (after drying)/200 ml; Standard solution: Cl$^-$ 8 mg/l and Cl$^-$ 6 mg/l (for calibration curve by two concentration points); Detector: Electrical conductivity detection; Column: AS12A (4×200 mm, DIONEX), AG12A (4×50 mm, DIONEX); Column temperature: Constant temperature of about 35° C.; Mobile phase: DIONEX anion-exchange eluent AS12A (2.7 mmol/l $Na_2CO_3$/0.3 mmol/l $NaHCO_3$), Flow rate of mobile phase: 1.5 ml per minute; Injection volume of the solution: 25 µl. The results are shown in Table 7 The chloride content was 19.66%.

TABLE 7

Analytical result of assay for chloride

| | Run 1 | Run 2 | Run 3 | Average | Reported value |
|---|---|---|---|---|---|
| Chloride content | 19.55% | 19.70% | 19.73% | 19.66% | 19.7% |

Based on the calculation in Table 8, it is considered that the number of hydrochloride units in arbekacin hydrochloride is 3.5 to 4.0.

TABLE 8

Theoretical value of hydrochloride content in arbekacin hydrochloride

| Number (x) of hydrochloride units | Molecular weight of chloride [g/mol] | Total molecular weight [g/mol] | Content of chloride [%] |
|---|---|---|---|
| 3.5 | 124.08550 | 680.23225 | 18.24 |
| 3.6 | 127.63080 | 683.87834 | 18.66 |
| 3.7 | 131.17610 | 687.52444 | 19.07 |
| 3.8 | 134.72140 | 691.17053 | 19.49 |
| 3.9 | 138.26670 | 694.81663 | 19.89 |
| 4.0 | 141.81200 | 698.46272 | 20.30 |

Molecular formula of arbekacin hydrochloride: $C_{22}H_{44}N_6O_{10}$ × HCl
Molecular weight of arbekacin free base: 552.61896 g/mol, molecular weight of chloride: 35.453 g/mol Example 3

Comparison of Arbekacin Sulfate and Arbekacin Hydrochloride Solutions in a Guinea Pig Cough Model A guinea-pig cough induction model was used to investigate differences in cough induction between the sulfate and hydrochloride forms of arbekacin. The tested substances were commercially available arbekacin sulfate (ABK—$H_2SO_4$) and arbekacin hydrochloride (ABK—HCl) that was prepared from arbekacin free base according to the method described in Example 2. The concentration of dosing solutions was set to be 25 mg/ml. In addition, physiological saline was used as a negative control agent whereas citric acid (30 mg/ml) was used as a positive control agent.

Male Hartley strain guinea pigs were subjected to the experiment, with 10 animals per group. A guinea pig with a flexible thin rubber plate attached at the neck was fixed inside a box composed of two chambers, which were ventilated by aspirating at a constant flow rate using a suction pump (PUL123-KS-650, M-I-P-S Corporation). Cough was detected on the basis of the following indicators: observation of symptoms, analysis of a respiration pattern in the soma-side by a double-flow plethysmograph method using a multi-functional respiration measuring device (Win Pulmos-I, M-I-P-S Corporation), and pressure changes in head-side and soma-side chambers measured by a pressure transducer (blood pressure monitoring kit, Japan Becton, Dickinson and Company). The case, in which a motion of coughing in the symptom observation was noted together with typical changes in the pressure in the head-side and soma-side chambers and in the respiration pattern of the soma side at the time of coughing, was determined to be a cough reflex. The test substances were nebulized using an electronic vibrating membrane nebulizer (eFlow®, PARI Pharma GmbH) and the aerosol was introduced into the head-side chamber so that a guinea pig under spontaneous breathing inhaled it for 10 minutes. Then, the occurrence of cough reflex was counted.

The results are shown in Table 9. Each value represents mean±standard deviation, n=10.

The arbekacin concentrations used in this example are not according to the invention.

TABLE 9

Number of coughs during 10 min after exposing guinea pigs to inhaled substances

| Substance | Dose (mg/ml) | Cough reflex (counts/10 min) |
|---|---|---|
| Saline | — | 0.9 ± 1.3 |
| Citric Acid | 30 | 20.1 ± 6.3 [1] |
| Arbekacin sulfate | 25 | 8.7 ± 6.3 |
| Arbekacin hydrochloride | 25 | 3.5 ± 2.0 [2] |

[1] Wilcoxon's rank sum test: saline vs citric acid: $P < 0.001$
[2] Wilcoxon's rank sum test: arbekacin sulfate vs arbekacin hydrochloride: $P < 0.05$ Compared to the physiological saline group, the number of occurrence of cough reflex in the citric acid group was significantly higher. With respect to arbekacin, the number of occurrence of cough reflex was significantly lower in the hydrochloride group than in the sulfate group.

Thus, it was demonstrated that, regarding arbekacin, cough induction by the hydrochloride form was weaker than that by the sulfate form.

Example 4

150 mg/ml and 100 mg/ml Arbekacin Hydrochloride Solution from Arbekacin Base 0.9 g of arbekacin base was dissolved in 4 g of a 0.5% (w/w) sodium chloride solution, resulting in a very alkaline solution with a pH of 10.96. The pH was adjusted to 6.77 using hydrochloric acid (32% (w/w) HCl solution) and 0.5% (w/w) sodium chloride solution was added until a final weight of 6 g. The ratio of the molar amount of chloride ions to the molar amount of arbekacin was approximately 3.7:1.

The formulation was sterile filtered under aseptic conditions. The osmolality of the formulation was 1379 mOsmol/kg, which is rather high. However, upon inhalation, the formulation was unexpectedly tolerated much better compared to the arbekacin sulfate based formulation described in Example 1. The chloride based formulation did not induce a cough reflex.

1 ml of the above formulation of 150 mg/ml was diluted with 0.5 ml of 0.9% (w/w) sodium chloride solution, resulting in a 100 mg/ml arbekacin formulation based on arbekacin chloride. The dilution with 0.9% (w/w) sodium chloride solution leads to a calculated ratio of the molar amount of chloride ions to the molar amount of arbekacin of approximately 4:1.

Also this formulation was tolerated better compared to the arbekacin sulfate formulation described in Example 1 and did not induce a cough reflex.

Example 5

Evaluation of Different Ratios of the Molar Amount of Chloride Ions to the Molar Amount of Arbekacin Four formulations with different ratios of the molar amount of chloride ions to the molar amount of arbekacin (free base) were prepared as shown in Table 10. All formulations contained 150 mg/ml arbekacin free base.

TABLE 10

Physicochemical properties of arbekacin formulations with different ratios of the molar amount of chloride ions to the molar amount of arbekacin (ratio Cl:ABK)

| | Formulation A pH adjusted with HCl | Formulation B pH adjusted with HCl and 2.75% (w/v) $H_2SO_4$ | Formulation C pH adjusted with HCl and 5.8% (w/v) $H_2SO_4$ | Formulation D pH adjusted with $H_2SO_4$ |
|---|---|---|---|---|
| Arbekacin base | 15 g | 15 g | 15 g | |
| Arbekacin sulfate [3] | | | | 21 g |
| NaCl | 0.25 g | 0.25 g | 0.25 g | 0.25 g |
| HCl [1] | 15.00 g | 9.28 g | 2.55 g | |
| $H_2SO_4$ [2] | | 2.75 g | 5.80 g | 0.86 g |
| NaOH 1N | q.s. | q.s. | q.s. | q.s. |
| Aqua pur. | ad 100 ml | ad 100 ml | ad 100 ml | ad 100 ml |
| Ratio Cl:ABK | 5.17:1 | 3.16:1 | 0.98:1 | 0.16:1 |
| Ratio Sulfate:ABK | 0:1 | 0.98:1 | 2.07:1 | ~2.5:1 |
| pH | 5.30 | 5.44 | 5.24 | 5.19 |
| Osmolality [mOsmol/kg] | 1291 | 947 | 578 | 362 |

TABLE 10-continued

Physicochemical properties of arbekacin formulations with different ratios of the
molar amount of chloride ions to the molar amount of arbekacin (ratio Cl:ABK)

|  | Formulation A pH adjusted with HCl | Formulation B pH adjusted with HCl and 2.75% (w/v) $H_2SO_4$ | Formulation C pH adjusted with HCl and 5.8% (w/v) $H_2SO_4$ | Formulation D pH adjusted with $H_2SO_4$ |
|---|---|---|---|---|
| Optical appearance | Clear solution, free of particles | Clear solution, free of particles | Clear solution, free of particles | Clear solution, free of particles |

[1] Concentration of HCl solution used for pH adjustment: 32% (w/w)
[2] Concentration of $H_2SO_4$ solution used for pH adjustment: 95-98% (w/w)
[3] Potency of arbekacin sulfate is 716 µg/mg. 21 g of arbekacin sulfate corresponds to 15 g arbekacin base.

Three male volunteers inhaled all four formulations with an eFlow® electronic vibrating membrane nebulizer (PARI Pharma GmbH) in a blinded experiment. All volunteers experienced immediate coughing upon inhalation of Formulation D. Formulations A, B, and C were much better tolerated than Formulation D. The test persons did either not describe adverse effects at all or only mentioned minor and tolerable cough for these three formulations.

The same volunteers participated in the experiment described in Example 1 and reported that Formulations A, B, and C were better tolerable than the formulation of Example 1 which only contained 100 mg/ml arbekacin. The better tolerability upon inhalation of Formulations A, B and C compared to Formulation D was related to the higher ratio of the molar amount of chloride ions to the molar amount of arbekacin.

Example 6

Therapeutic Effect of Arbekacin Inhalation on Experimental Pneumonia Caused by *Pseudomonas aeruginosa* in Neutropenic Mice The therapeutic effect of arbekacin inhalation on experimental pneumonia in neutropenic mice, caused by *P. aeruginosa*, was compared with the therapeutic effect of amikacin and tobramycin.

Cyclophosphamide (Sigma-Aldrich Co.) was dissolved in physiological saline. Four to five week-old Crlj:CD1(ICR) male mice were immunosuppressed by intraperitoneal injection of 150 and 100 mg/kg of cyclophosphamide solution 4 days and 1 day before infection, respectively. Thereafter, pulmonary infection was induced by intranasal inoculation of amikacin- and tobramycin-resistant *P. aeruginosa* having the aac(6)-lae encoding an aminoglycoside modifying enzyme. The antibiotics dissolved in saline were administered to each mouse using an electronic vibrating membrane nebulizer (eFlow®, PARI Pharma GmbH, spray flow rate: approximately 0.5 ml/min) two hours after the infection, and viable cells per lung were counted 20 hours after the infection. As for the doses of arbekacin, three levels were set at 3, 10 and 30 mg/ml, and the respective doses of amikacin and tobramycin were at three levels of 10, 30, and 100 mg/ml. The inhalation duration was five minutes. Meanwhile, physiological saline was administered to a non-treatment control group. The results are shown in Table 11.

The results show that arbekacin, amikacin, and tobramycin significantly decreased the viable cell counts in the lung at all the dose levels in comparison to the non-treatment control group. Furthermore, the therapeutic effect of arbekacin was significantly superior to those of amikacin and tobramycin at the same dosage (10 or 30 mg/ml).

The arbekacin concentrations used in this example are not according to the invention.

TABLE 11

Therapeutic effect of different antibiotics in a mouse model [1] of respiratory infection caused by an amikacin- and tobramycin-resistant *P. aeruginosa* strain [2]

| Test group | Level of drug (mg/ml) | Number of intrapulmonary viable cells ($\log_{10}$ CFU/lung)[3] | Test result (compared to non-treatment control group[4]) | Test result (compared to amikacin[4]) | Test result (compared to tobramycin[4]) |
|---|---|---|---|---|---|
| Non-treatment control group | — | 6.90 ± 0.41 | n.a. | n.a. | n.a. |
| Arbekacin | 3 | 4.07 ± 2.18 | 1 ≤ 0.01 | n.a. | n.a. |
|  | 10 | 2.20 ± 0.99 | 1 ≤ 0.001 | P ≤ 0.01 | P ≤ 0.01 |
|  | 30 | 1.98 ± 0.83 | 1 ≤ 0.001 | P ≤ 0.01 | P = 0.10 |
| Amikacin | 10 | 5.65 ± 1.55 | 1 ≤ 0.01 | n.a. | n.a. |
|  | 30 | 4.46 ± 1.68 | 1 ≤ 0.001 | n.a. | n.a. |
|  | 100 | 2.65 ± 1.74 | 1 ≤ 0.001 | n.a. | n.a. |
| Tobramycin | 10 | 5.74 ± 1.57 | P < 0.05 | n.a. | n.a. |
|  | 30 | 3.48 ± 1.85 | 1 ≤ 0.001 | n.a. | n.a. |
|  | 100 | 3.53 ± 1.88 | 1 ≤ 0.001 | n.a. | n.a. |

[1] Mouse model: Crlj:CD1(ICR) male mouse, 10 mice per group
[2] Strain used: *P. aeruginosa* MSC17707 (having the aac(6')-lae encoding an aminoglycoside modifying enzyme and resistant to amikacin and tobramycin)
[3] Average value ± standard deviation
[4] Steel test

Example 7

150, 125, and 100 mg/ml Arbekacin Hydrochloride Solutions from Arbekacin Base A further arbekacin hydrochloride formulation containing 150 mg/ml was prepared as in Example 4, but distilled water was used instead of the 0.5% (w/w) sodium chloride solution. The pH of the solution was adjusted to 7.15 with a 32% (w/w) HCl solution. Although the formulation of Example 4 was well-tolerated, the omission of NaCl allows to somewhat reduce the osmolality of the formulations, thereby further improving their tolerability. The osmolality measured in the final formulation was 1091 mOsmol/kg. The ratio of the molar amount of chloride ions to the molar amount of arbekacin was approximately 3.5:1.

Subsequently, two dilutions of this formulation were made with distilled water. This resulted in a formulation with 125 mg/ml arbekacin and an osmolality of 882 mOsmol/kg and a solution with 100 mg/ml arbekacin and an osmolality of 680 mOsmol/kg. The ratio of the molar amount of chloride ions to the molar amount of arbekacin in these formulations was also approximately 3.5:1.

Example 8

Formulations of Arbekacin Hydrochloride for Inhalation

For an improvement of dispensability and lubrication of surfaces, arbekacin hydrochloride salt formulations may additionally contain a surfactant being of ionic or non-ionic nature. Compositions containing in addition different surface tension-reducing excipients are compiled in the table below.

TABLE 12

Aqueous formulations of arbekacin hydrochloride for inhalation

| Formulation | 1 | 2 | 3 |
|---|---|---|---|
| Arbekacin base | 12 g | 12 g | 12 g |
| Na-EDTA | 0.02 g | 0.02 g | 0.02 g |
| Polysorbate 80 | 0.05 g | — | — |
| Lecithin | — | 0.02 g | — |
| Vitamin E TPGS | — | — | 0.03 g |
| NaCl | 0.20 g | 0.20 g | 0.20 g |
| HCl | q.s. ad pH 5.0 | q.s. ad pH 5.0 | q.s. ad pH 5.0 |
| Aqua purificata | ad 100 ml | ad 100 ml | ad 100 ml |

Example 9

150 mg/ml Arbekacin Hydrochloride Solution with pH 3

15.0 g arbekacin base and 0.25 g NaCl were dissolved in approximately 70 g aqua purificata. The pH was adjusted to approximately 3 using hydrochloric acid (32% w/w) and 1 N sodium hydroxide solution. Aqua purificata was added up to 100 ml after pH adjustment and the formulation was characterized physicochemically. The pH of the resulting formulation was 3.1. The formulation had an osmolality of 1288 mOsmol/kg, the surface tension was 73.62 mN/m and a viscosity of 1.81 mPa·s was measured. The formulation was a clear solution, that was free of particles.

Example 10

Determination of Osmolality

To compare the osmolality of the hydrochloride salt and the sulfate salt of arbekacin, aqueous solutions of arbekacin hydrochloride and arbekacin sulfate were prepared with an arbekacin free base concentration of 150 mg/ml. While distilled water was used for dissolving arbekacin free base in test A, 0.25% (w/w) aqueous sodium chloride solution was used in test B. The prepared solutions were divided into different aliquots that were pH adjusted by either hydrochloric acid or sulfuric acid (resulting in arbekacin hydrochloride solutions and arbekacin sulfate solutions, respectively) to obtain solutions with a pH of about 8.0, 7.0, 6.5, and 5.7. The osmolality of these solutions was measured. Additionally, the osmolality was measured in a mixture of these arbekacin hydrochloride and arbekacin sulfate solutions (ratio 9:1; same pH solutions were mixed) to evaluate the osmolality changes by adding arbekacin sulfate solution to arbekacin hydrochloride solution.

TABLE 13

Osmolality and pH of arbekacin solutions when using distilled water for dissolving arbekacin free base (test A)
Ratio of arbekacin hydrochloride solution to arbekacin sulfate solution

| 100:0 | | 90:10 | | 0:100 | |
|---|---|---|---|---|---|
| Osmolality | pH | Osmolality | pH | Osmolality | pH |
| 918 | 7.95 | 862 | 8.04 | 359 | 8.09 |
| 1009 | 7.05 | 944 | 7.16 | 304 | 7.20 |
| 1073 | 6.51 | 986 | 6.49 | 281 | 6.67 |
| 1263 | 5.72 | 1160 | 5.72 | 280 | 5.86 |

TABLE 14

Osmolality and pH of arbekacin solutions when using 0.25% (w/w) aqueous sodium chloride solution for dissolving arbekacin free base (test B Ratio of arbekacin hydrochloride solution to arbekacin sulfate solution

| 100:0 | | 90:10 | | 0:100 | |
|---|---|---|---|---|---|
| Osmolality | pH | Osmolality | pH | Osmolality | pH |
| 977 | 8.08 | 928 | 8.09 | 438 | 8.07 |
| 1101 | 7.16 | 1028 | 7.17 | 375 | 7.26 |
| 1150 | 6.47 | 1066 | 6.49 | 356 | 6.60 |
| 1171 | 5.75 | 1091 | 5.75 | 374 | 5.78 |

Example 11

100 mg/ml Formulations of Arbekacin

Formulations of 100 mg/ml Arbekacin were prepared using a mixture of hydrochloric acid (HCl) and sulphuric acid ($H_2SO_4$) to adjust the pH as shown in Table 15. Formulation B additionally contained 0.25% of NaCl. The Formulations were characterized regarding their osmolality, pH and visual appearance.

TABLE 15

100 mg/ml formulations of Arbekacin

|  | Formulation A | Formulation B |
|---|---|---|
| Ratio Cl:ABK | 0.85 | 1.09 |
| Arbekacin base | 10 g | 10 g |
| NaCl | — | 0.25 |
| HCl (32% w/w) | 1.76 | 1.76 |
| H$_2$SO$_4$ (95-98% w/w) | 3.94 | 3.94 |
| NaOH 1N | q.s. | q.s. |
| Aqua purificata | Ad 100 ml | Ad 100 ml |
| pH (after adjustment) | 5.29 | 5.29 |
| Osmolality [mOsmol/kg] | 336 | 411 |
| Optical appearance | Clear solution, free of particles | Clear solution, free of particles |

The invention claimed is:

1. An aqueous liquid pharmaceutical composition comprising arbekacin and chloride ions, wherein the concentration of arbekacin, calculated as free base, is at least 100 mg/ml and the ratio of the molar amount of chloride ions to the molar amount of arbekacin is at least 0.9 : 1.

2. The aqueous liquid pharmaceutical composition according to claim 1, wherein the molar amount of sulfate ions in the composition is no greater than 200 mol-% of the molar amount of arbekacin.

3. The aqueous liquid pharmaceutical composition according to claim 1, wherein the ratio of the molar amount of chloride ions to the molar amount of arbekacin is at least 3 : 1.

4. The aqueous liquid pharmaceutical composition according to claim 3, wherein the ratio of the molar amount of chloride ions to the molar amount of arbekacin is at least 5 : 1.

5. The aqueous liquid pharmaceutical composition according to claim 1, wherein the composition is substantially free of sulfate ions.

6. The aqueous liquid pharmaceutical composition according to claim 1, wherein the composition has an osmolality of at least 350 mOsmol/kg.

7. The aqueous liquid pharmaceutical composition according to claim 1, wherein the composition has an osmolality of 550 to 1500 mOsmol/kg.

8. The aqueous liquid pharmaceutical composition according to claim 1, wherein the composition has a pH of 3 to 7.

9. The aqueous liquid pharmaceutical composition according to claim 1, wherein the composition has a pH of 5 to 7.

10. The aqueous liquid pharmaceutical composition according to claim 1, wherein the arbekacin is either molecularly or colloidally dissolved.

11. A method for the treatment or prevention of a disease of the upper or lower respiratory tract, wherein the method for the treatment or prevention of the disease comprises the step of aerosolizing the aqueous liquid pharmaceutical composition of claim 1 and letting a patient inhale the aerosol thus produced.

12. Arbekacin hydrochloride in solid salt form.

* * * * *